United States Patent [19]

Jones

[11] 3,963,421

[45] June 15, 1976

[54] TLC METHOD FOR DRUG DETECTION

[75] Inventor: Donald W. Jones, Auburn, Calif.

[73] Assignee: Sierra Laboratories, Inc., Auburn, Calif.

[22] Filed: July 12, 1974

[21] Appl. No.: 487,957

[52] U.S. Cl. .......................... 23/230 B; 23/253 TP; 73/61.1 C; 210/31 C
[51] Int. Cl.² ................. B01D 15/08; G01N 31/08; G01N 33/16
[58] Field of Search .................... 23/230 B, 253 TP; 210/31 C; 73/61.1 C

[56] References Cited
UNITED STATES PATENTS

| | | | |
|---|---|---|---|
| 3,275,416 | 9/1966 | Zaar | 23/230 B |
| 3,540,850 | 11/1970 | Halpaap | 23/230 B |
| 3,714,035 | 1/1973 | Jones | 210/31 C |
| 3,832,134 | 8/1974 | Sohn | 23/253 TP |

OTHER PUBLICATIONS

"Isolation & Identification of Drugs," E. G. C. Clarke, ed., pp. 16–30, Pharmaceutical Press, London, 1969.

Primary Examiner—Morris O. Wolk
Assistant Examiner—Sidney Marantz
Attorney, Agent, or Firm—Townsend and Townsend

[57] ABSTRACT

A simplified method of carrying out thin-layer chromatography for the detection of drugs. Neutral, basic amine-containing, and acidic drugs are extracted from a physiological medium with a salt-organic solvent system. The organic phase is then transferred incrementally to a small dish having a small adsorbent disc, with the organic solvent system evaporated between the incremental additions. When the organic extractant is substantially completely evaporated, the disc is then introduced into an available opening adjacent one end of a thin-layer chromatograph. The chromatograph is then developed employing a developing solution. After drying the chromatograph, the chromatograph is subjected to specific reagent treatment and developing processes, involving dipping, rather than spraying, to color the various spots and make them visible. In this manner, a physiological sample can be rapidly treated and the presence of a drug determined in accordance with its migration and coloration under reagent treatment.

11 Claims, No Drawings

TLC METHOD FOR DRUG DETECTION

BACKGROUND OF THE INVENTION

1. Field of the Invention

Thin-layer chromatography is a versatile and economical method for the determination in physiological media of a wide variety of drugs. The field of thin-layer chromatography has been extensively researched, and many techniques and reagents have been developed for the detection of drugs. One technique is exemplified in U.S. Pat. No. 3,714,035. This technique involves the scoring of a chromatograph to leave an opening in which a disc may be introduced. The disc is impregnated with the sample to be analyzed. By having additional scored areas, standards can be introduced into the other scored areas, which have known amounts of specific drugs. By developing the sample and standard simultaneously on the same chromatograph, one can compare the sample spots to the standard spots and make an accurate determination of whether a specific drug is present.

While the use of the disc greatly simplifies thin-layer chromatography, there are still problems in insuring satisfactory extraction of the drug from the physiological sample, accurate transfer of the drug to the disc, and methods which allow for discrimination between drugs of similar structure, which may have similar migratory aptitudes. There is, therefore, a need to improve methods of preparing the sample disc and developing the chromatograph to allow for rapid and accurate discrimination among a wide variety of drugs of similar structures or similar responses to various reagents.

2. Description of the Prior Art

Articles and texts of interest include Kaye, Handbook of Emergency Toxicology, 3rd Edition, Charles C. Thomas, Springfield, Illinois, 1970; Curry, Poison Detection in Human Organs, 2nd Edition, Charles C. Thomas, Springfield, Illinois, 1969; Davidow, et al., A Thin-Layer Chromatographic Screening Procedure for Detecting Drug Abuse, The American Journal of Clinical Pathology, 38, 714 (1968); Dole, et al., Detection of Narcotic Drugs, Tranquilizers, Amphetamines and Barbiturates in Urine, J.A.M.A., 198, 349 (1966); Fujimoto, et al., Toxicology of Applied Pharmacology, 16, 186 (1970); Mule, Journal of Chromatography, 39, 302 (1969); Sunshine, et al., Clinical Chemistry, 16, 11 (1970); Weissman, et al., Clinical Chemistry, 17, 875 (1971); Jones, et al., Drug Detection by TLC, Comparative Study, California Association of Criminalists, Menlo Park, California, October 1973; and Jones, et al., An Improved Method for the Detection of Phenothiazines, Annual Meeting, CAP-ASCP, Chicago, Illinois, October 1973.

SUMMARY OF THE INVENTION

A method is provided for rapidly and accurately detecting the presence of a wide variety of basic amine, acidic and neutral drugs, employing a thin-layer chromatograph. The method employs extracting a sample from the physiological medium with a salt-organic extractant solvent system; transferring incrementally the organic extractant to an evaporating dish having a small absorbent disc and substantially completely evaporating the organic extractant after each addition at a mildly elevated temperature; transferring the resulting disc to a scored area adjacent one end of a thin-layer chromatograph, preferably having one or more additional discs aligned with the sample disc having known amounts of one or more drugs as standards; developing the chromatograph with a developing solution, so as to have any drugs present migrate from the discs; drying the chromatograph and treating the chromatograph by dipping into one or more reagent solutions, so as to color the spots which are formed to provide distinctive colorations for the various drugs.

Specific extractants, developing solutions and treating reagents are provided, depending upon whether the drugs are basic or neutral.

DESCRIPTION OF THE SPECIFIC EMBODIMENTS

A chromatographic method is provided for rapidly determining acidic, aromatic basic amine-containing drugs and neutral drugs. Normally, the physiological sample will be either urine or serum, depending upon the drug of interest. The sample is introduced into an extraction vessel or zone containing a salt-halocarbon organic extractant solvent system--aqueous sat. $ZnCl_2$ for acidic and neutral drugs; granular sodium tungstate or molybdate for basic and neutral drugs--whereby the halocarbon organic extractant is of lower density than the final aqueous solution. After agitating the vessel, so as to enhance the transfer of the drug or drugs of interest to the organic extractant, the organic extractant is then transferred to a small evaporating dish of convenient size.

In the evaporating dish is a small absorbent disc which serves to absorb the drug substantially completely. The transfer of the organic extractant is carried out incrementally, whereby substantially all of the solvent is evaporated before a subsequent addition, by maintaining the evaporating dish at a mildly elevated temperature. It is found that this method of evaporation results in the substantially complete transfer of any drug contained in the organic extractant to the small absorbent disc.

A thin-layer chromatograph is employed which has a substantially inert support. Conveniently, the support is glass fiber or other inert material which can withstand sulfuric acid treatment and will not interfere with the development of the chromatograph. The chromatograph has one or more scored areas which are aligned adjacent one end of the chromatograph. One of the scored areas, normally the centrally scored area, is for receiving the sample absorbent disc. The other scored areas are used for introducing absorbent discs which are employed as standards and have known amounts of specific drugs. Therefore, when the chromatograph is developed, the spot resulting from the sample disc can be compared to the spot resulting from the standard discs and compared as to color and distance of migration ($R_f$).

After inserting the dry absorbent disc into the chromatograph, the chromatograph is developed by conventional means. The chromatograph is introduced into a chromatography jar having a small amount of developing solution. As the developing solution moves up the chromatograph, the various drugs will migrate from the disc upwards with the solvent. After a sufficient time for the development of the chromatograph, the chromatograph is removed from the chromatography jar and the solvent evaporated to leave a dry chromatograph.

Depending on the drug or drugs of interest, the chromatograph is now treated according to prescribed protocols, which results in the visualization of specific spots. The protocols do not involve spraying, but rather dipping, which greatly enhances the ease with which the spots can be detected. By comparing the spots of the sample, as to size and color, with the spots of the standards, one can make a semi-quantitative determination of the approximate amount of the particular drug in the sample.

The three classes of drugs which can be readily determined are: (1) those having a basic amine group which may be aliphatic or heterocyclic and will normally have a carbocyclic aromatic ring; (2) neutral drugs; and (3) acidic drugs. The drugs of interest act on the central nervous system, with the last group being primarily hypnotics and sedatives, while the former groups include narcotics and analgesics, central nervous system stimulants, and various tranquilizers. See Goodman and Gilman, The Pharmacological Basis of Therapeutics, 3rd Edition, The MacMillan Company (1969).

The drugs of interest which are basic have a wide variety of different chemical structures. A number of the drugs are alkaloids, which includes opiates, such as morphine and codeine, strychnine, quinine, cocaine, nicotine, and the like.

Another class of drugs are the phenothiazines, such as chlorpromazine, trifluoperazine, triflupromazine, and the like.

Another group of compounds are the aralkylamines, such as methadone, propoxyphene, amphetamine, methamphetamine, and the related compound meperidine (where the amine nitrogen is part of a saturated ring).

An additional group of compounds are the dibenzazepines, such as imipramine and the structurally related dibenzheptadienes, such as amitriptyline.

Another class of compounds are the benzodiazepine compounds, such as chlordiazepoxide and diazepam.

Other drugs which have a basic amine include methaqualone, which is a benzpyridazine and Sinequan (doxepin) which is an aminoalkyl dibenzoxepin.

Extracted along with the basic amine compounds is meprobamate which is a neutral compound and a carbamate ester.

The compounds which are primarily hypnotics and sedatives and are primarily acidic are for the most part lactams having one or more amide groups. For the most part, these compounds will have the following formula:

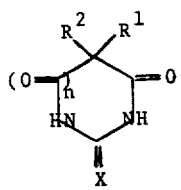

wherein
X is $H_2$, oxygen or sulfur;
$n$ is 0 or 1;
$R^1$ and $R^2$ are hydrocarbon of from 1 to 8 carbon atoms having from 0 to 1 site of ethylenic unsaturation, and may be aliphatic, alicyclic or aromatic, with the proviso that when $n$ is 0, $R^1$ and $R^2$ are phenyl and when X is hydrogen, $R^1$ is phenyl and $R^2$ is ethyl.

Drugs included within the above formula are diphenylhydantoin, phenobarbital, secobarbital, pentobarbital, amobarbital, aprobarbital and thiopental.

Included among the neutral drugs are ethinamate, (1-ethlnylcyclohexyl)carbamate, glutethimide and ethchlorvynol.

In carrying out the subject process for the detection of the above and similar drugs, an extraction zone is employed. The extraction zone contains a salt either as a solid or a salt solution plus an organic solvent mixture. The final aqueous phase has a density greater than the halocarbon containing organic extracting solvent. Thus, upon extraction, the organic layer, after separation, is on the top of the aqueous layer.

When extracting for the basic amine-containing drugs (including certain neutral drugs), the aqueous solution will include a heavy complex anion water soluble salt which is stable at alkaline pH, and sodium chloride in sufficient amount to provide a buffered solution having a pH of about 9 to 9.5, usually about 9.3, and a density greater than the organic extractant. Of particular interest are the alkali metals, e.g. sodium and potassium tungstate and molybdate. Tungstate will be referred to as exemplary. The amount of tungstate will be at least about 25 weight percent of the aqueous solution after addition of the sample, and usually not more than about 70 weight percent, preferably being about 30 to 60 weight percent. The amount of salt can vary more widely, since it serves to increase the density of the aqueous solution, as well as having a salting out effect, and will generally be about 5 to 15 weight percent, more usually about 8 to 12 weight percent.

The organic extractant is conveniently a mixture of chloroform with other organic solvents, normally a mixture of polar and nonpolar solvents. Usually, the organic extractant will have from about 40 to 60 volume percent of chloroform, combined with aliphatic hydrocarbons of from 4 to 8 carbon atoms, preferably about 6 to 7 carbon atoms, and an alkanol of from 3 to 4 carbon atoms, more usually 3 carbon atoms. The alkanol generally will be from about 15 to 20 volume percent, while the aliphatic hydrocarbon solvent will generally be from about 25 to 40 volume percent, more usually from about 30 to 35 volume percent.

the volume ratio of the organic extractant to the aqueous sample solution will generally be from about 1.5 to 5 parts by volume of organic extractant to 5 parts by volume of the aqueous solution, more usually from about 2 to 5 parts by volume of organic extractant per 5 parts by volume of aqueous sample solution.

Conveniently, the urine samples are added to a vial containing the salts or salt solution and the organic extractant. The salts rapidly dissolve into the aqueous urine sample.

When extracting for acidic drugs, the reagents will differ in that the sample will be diluted with a saturated aqueous zinc chloride solution, at an acidic pH, below about 4, usually above 2, preferably about 3. Generally, the sample will be blood serum and will be diluted 2 to 3 fold with the aqueous solution, so that the final solution will be less than saturated. The concentration of zinc chloride will generally be about 150 to 375g per 100ml at about room temperature.

The organic extractant employed for the acidic drugs has the same general composition as indicated for the basic amine drugs.

The aqueous and organic layers are then agitated vigorously for a few minutes, generally from about 1 to 5 minutes, more usually from about 2 to 3 minutes, and centrifuged for a few minutes to insure accurate separation. A conventional centrifuge can be employed and the centrifugation carried out at about 1,000 to 5,000 r.p.m.

A small evaporating plate is now employed to which the organic extractant is transferred incrementally, generally in from about 3 to 10 aliquots. The evaporating plate should be sufficient to accommodate the individual volumes transferred. Contained in the evaporating plate is a small absorbent disc for introduction into the chromatograph. The absorbent disc will generally be from about 1/32 to about ¼ of an inch in diameter and of a few mils in thickness, normally being the thickness of conventional thin-layer chromatographs. The disc will be of the same material as the chromatograph, having an inert fibrous support, such as glass fiber, and an absorbent material such as alumina or silica, preferably silica impregnated into the fibers.

To enhance the rate of evaporation, the plate will normally be warmed to above about 40°C and less than about 80°C, generally being from about 50°C to 75°C. After each addition of an aliquot of the organic extractant, substantially all or all of the organic extractant is evaporated before the next addition. It is found by this method of addition of the organic extractant and evaporation, substantially all of the drug of interest is absorbed by the disc with very little remaining on the surface of the evaporating plate.

The sample disc is now ready to be transferred to a chromatograph. The chromatograph employed is described in U.S. Pat. No. 3,714,035. The chromatograph has one or more scored areas near one end of the chromatograph for acceptance of the sample disc and standard discs as desired. The sample disc is carefully transferred to the chromatograph. Where a plurality of scored areas are provided, usually the sample will be introduced into the central scored area. Standard discs may then be introduced into the remaining scored areas, the standard discs having the same or different drugs.

The chromatographs which are employed are conveniently of from about 4.0 × 12cm, but may be of lesser or greater dimensions. The chromatograph is then introduced into a chromatography jar. While any developing fluid may be employed which has been previously disclosed in the literature for developing a particular drug, a particularly desirable developing fluid employs a combination of a major amount of ethyl acetate, a minor amount of ammonium hydroxide and a minor amount of a secondary organic solvent. A developing solution which has been found to be particularly advantageous combines about 1 part by volume of a mixture of ethyl acetate and methanol, having a ratio of ethyl acetate to methanol of about 20–40:1, usually 20–35:1, particularly about 96.5/3, with about 0.025 to 0.15, preferably about 0.025 to 0.075 part by volume of ammonium hydroxide of from about 4 to 6, preferably about 5M concentration.

For the acidic compounds, the developing fluid will generally have from about 5 to 15 volume percent of chloroform with the remainder being ethyl acetate, the mixture combined with from about 0.025 to 0.15, preferably about 0.05 to 0.1 part/part by volume of concentrated ammonium hydroxide.

With a chromatograph of the size indicated above, it is found satisfactory to use about 2ml of the developing solution, and allow for migration of the solution about 10cm from the immersed end of the chromatograph, a process which normally requires about 20 minutes.

At the end of this time, any drugs in the sample will have migrated a sufficient distance to provide the desired separation of the various drugs in the indicated categories.

Depending on whether the drug is in the basic group or the acidic group, different protocols will be employed to detect the spot.

For the basic group of compounds, the chromatograph is dried at a mildly elevated temperature, a warm air dryer being found satisfactory. The chromatograph is then treated with formaldehyde vapors. A convenient manner is to introduce the chromatograph into a jar containing 40% HCHO at a depth of one inch which is covered by a coarse screen to hold the chromatograph out of the fluid phase. (Vapors can be achieved by heating paraformaldehyde, employing a formalin solution or the like). The time for which the chromatograph is contacted with the formaldehyde may be varied widely, but a short contact time is preferred, usually from about 0.5 to about 2 minutes.

After the chromatograph has been treated with formaldehyde, it is then dipped into Mandelin's reagent. Mandelin's reagent employs ammonium metavanadate in concentrated sulfuric acid at a concentration of about 100mg% (100mg Vanadate in 100ml $H_2SO_4$) (mg% = mg/100ml solution). The chromatograph is merely dipped into the reagent and then removed and examined for any colored spots. The colored spots are recorded, and when standards are used, compared with the colored spots of the standard. The chromatograph is then washed with water, conveniently by being introduced under a tap of running water at room temperature and the chromatograph viewed as to any change in color or color produced. After further washing of the chromatograph and observing any color changes, the chromatograph is then introduced into Dragendorf's reagent containing 1% iodine (modified Dragendorf's reagent).

The chromatograph is left in the reagent for a short time, usually about one minute, then removed and observed as to any new spots which may have developed. Again, if standards have been employed, the spots developed from the sample disc may be compared with the standards.

Sometimes, additional information can be obtained by observing the chromatograph under ultraviolet light, both prior to introduction into the reagent solutions and the subsequent treatment. For example, quinine will fluoresce as a brilliant blue spot when examined initially, while both amphetamine and methamphetamine will show a brilliant blue fluorescence after the first water wash.

By employing the above technique, alkaloids, phenothiazines, dibenzoxepins, aralkylamines, e.g. methadone, propoxyphene, amphetamine, etc., as well as other drugs which have been indicated can be readily detected.

For the acidic group of drugs, primarily the narcotics and sedatives, a somewhat different protocol and different reagents are employed. After drying the chromatograph, the chromatograph is introduced into a chloroform solution containing 10mg% of diphenylcarbazone and 0.1 weight percent of diethylamine. The chromatograph is dipped in and out and then warmed for a minute or two to dry. The chromatograph is then dipped into a one weight percent aqueous silver salt, e.g. nitrate, acetate, etc., and retained in the solution until the height of maximum color development is achieved. This will generally be within a few seconds and the chromatograph is then rapidly transferred to a 2 weight percent aqueous mercuric sulfate solution into which it is dipped in and out, usually repeatedly, until maximum color has been developed. Any water soluble mercuric salt may be used which has an inert convenient anion, e.g. nitrate. The chromatograph is then rinsed under running water and allowed to dry with the various spots being observed and recorded. Where standards have been employed, the spot(s) from the sample may be compared to the spots from the standard.

Specific protocols have been established for the basic amine drugs and the acidic drugs. The following is the specific protocol for the basic amine drugs. An extraction vial is provided containing 2.5g of sodium tungstate, 0.5g of sodium chloride, and 3ml of a solution containing 50 volume percent chloroform, 17 volume percent isopropyl alcohol, and 33 percent heptane. 5ml of urine sample is added to the vial, the vial agitated vigorously for approximately 3 minutes and then centrifuged at 2,000–3,000 r.p.m. for about 3 minutes.

The supernatant organic phase is then incrementally transferred to a procelain evaporating plate (Coors 000) containing a blank disc of SA glass paper approximately ¼ inch in diameter. The evaporating plate is maintained at about 65°–70°C, with the well being almost completely filled each time and allowed to evaporate to substantial dryness.

The disc is then transferred to a scored SA glass paper 4.0 × 12cm chromatograph and developed in a chromatography jar having a mixture of 2ml of developing fluid and 100μl of ammonium hydroxide solution. The developing fluid is 96.5% ethyl acetate and 3.5% methyl alcohol by volume. The ammonium hydroxide solution is obtained from a mixture of 0.67ml concentrated ammonium hydroxide and 1.33ml water. The developing fluid is combined with the ammonium hydroxide just prior to use, is mixed for about 30 seconds and then introduced into the chromatography jar.

The chromatogram is developed by allowing the chromatograph to sit in the developing solution for about 20 minutes. The chromatograph is then removed from the chromatography jar, dried with warm air from a hair dryer, or placed on a surface of low heat, and then introduced into a formaldehyde jar having formalin in the bottom and a platform, whereby the chromatograph is subjected to the formaldehyde vapors, but is not introduced into the formalin solution. The chromatograph is allowed to remain in the vapors for about 60 seconds, is then removed from the formaldehyde jar and dipped into Mandelin's reagent, examined for colored spots, dipped rapidly into and out of a running stream of water, examined again, and then washed thoroughly in a running stream of tap water. The chromatograph is then dipped into the modified Dragendorf's reagent and allowed to remain in the reagent for approximately one minute, removed, washed in a rapid stream of tap water, and allowed to hang and dry. The various spots which develop are observed and recorded and preferably compared to standards.

For the neutral compounds, the protocol is modified in that the extraction vial contains 5ml of saturated zinc chloride solution, pH 3, and 3ml of a solvent containing by volume 50% chloroform, 17% isopropyl alcohol and 33% heptane. The sample will be only 2ml of either plasma or serum. The extraction and transfer to the disc is carried out as previously described.

After transferring the disc to the chromatograph as previously described, the chromatograph is introduced into a chromatography jar having 2ml of a solution by volume of 90% ethyl acetate and 10% chloroform and 150μl of concentrated ammonium hydroxide, which has been vortexed vigorously for about 30 seconds before introducing into the chromatography jar. The chromatograph is developed for about 20 minutes, removed from the chromatography jar, warmed so as to remove solvent and ammonia, and then dipped in and out of a chloroform solution containing 10mg percent diphenylcarbazone and 0.1 weight percent diethylamine.

After removal from the diphenylcarbazone reagent, the chromatograph is dried and then dipped into a one weight percent aqueous silver nitrate solution until the height of maximum color development is achieved, followed by immediate transfer into a 2 weight percent mercuric sulfate solution. The chromatograph is dipped repeatedly in the mercuric sulfate solution until maximum color has been developed, then rinsed under running water and hung up and allowed to dry. Where standards have been employed, the spots from the sample are compared to the standard spots.

In following the above protocol, a wide variety of drugs which have been indicated previously can be easily and efficiently separated and compared to known standards, so as to have a high degree of assurance of the identity of the drug. The subject protocol is particularly useful in small laboratories, where sophisticated equipment is unavailable, and yet the presence of a wide variety of drugs must be rapidly and accurately determined in diagnosing a patient. The method is simple, requires relatively few manipulative steps, the steps are easily carried out, and for the most part, do not require accurate measurements or extreme care in transfer.

The extraction can be readily carried out in a vial, where all the materials are initially introduced into the vial, so that only the sample need be introduced into the vial. The transfer to an evaporating dish is easily carried out and the evaporation step rapidly achieved. By this simple means, substantially quantitative transfer of the drug or drugs in the sample to a small absorbent disc is obtained. Normal chromatographic techniques may then be employed, followed by dipping into reagents which provide a broad range of coloration for drugs of substantially similar structure. Therefore, by comparison of the migration and coloration of a particular sample with standards of known drugs, one can detect to a high degree of confidence, a wide variety of different drugs.

Although the foregoing invention has been described in some detail by way of illustration and example for purposes of clarity of understanding, it will be obvious that certain changes and modifications may be practiced within the scope of the appended claims.

What is claimed is:

1. A thin-layer chromatographic method for detecting acidic, basic amine-containing or neutral drugs in a physiological medium which comprises:

agitating with a halocarbon-containing organic extractant an aqueous water-soluble inorganic salt-containing solution containing said physiological medium at a selected pH, wherein the amount of said salt is sufficient to provide a density of said aqueous medium greater than said organic extractant, whereby a substantial proportion of any of said drug is transferred to said organic extractant, said organic extractant consisting essentially of 40–60 volume percent chloroform, 15–20 volume percent alkanol of from 3 to 4 carbon atoms and 25 to 40 volume percent of an aliphatic hydrocarbon solvent of from 4 to 8 carbon atoms and the volume ratio of organic extractant to aqueous solution being in the range of 1–5:5;

incrementally transferring substantially free of said aqueous solution said organic extractant to an evaporating zone at a mildly elevated temperature containing a small absorbent disc, whereby a substantial proportion of said extractant is evaporated after each addition until completely evaporated and any of said drug present in said extractant is substantially quantitatively transferred to said disc;

introducing said disc into a scored area adjacent one end of a thin-layer chromatographic plate and developing said thin-layer chromatographic plate using a polar organic developing solvent containing a small amount of ammonium hydroxide;

drying said thin-layer chromatographic plate and treating the dry thin-layer chromatographic plate with reagents for modifying the appearance of any of said drugs, so that colors characteristic of said drugs are produced.

2. A method according to claim 1, wherein said thin-layer chromatographic plate has a plurality of scored areas equally distant from one end of said chromatographic plate and at least one absorbent disc containing predetermined amounts of known drugs is introduced into at least one of said scored areas, whereby said drugs migrate during said development of said chromatographic plate and provide a standard for comparison.

3. A method according to claim 1, wherein said chromatographic plate has a silica absorbent on a glass fiber support.

4. A method according to claim 3, wherein said polar organic developing solvent has a major amount of ethyl acetate.

5. A method according to claim 1, wherein said absorbent disc is of from about 1/32 to ¼ inch in diameter and is composed of silica gel on a glass fiber support.

6. A chromatographic method for detecting basic amine-containing and neutral drugs, in a physiological medium, which comprises:

agitating with a halocarbon-containing organic extractant an aqueous solution of said physiological medium containing an inorganic salt to produce a mildly basic pH and having a sufficient amount of said inorganic salt to have a density greater than said organic extractant to transfer any of said drug to said extractant said organic extractant consisting essentially of 40–60 volume percent chloroform, 15–20 volume percent alkanol of from 3 to 4 carbon atoms and 25 to 40 volume percent of an aliphatic hydrocarbon solvent of from 4 to 8 carbon atoms and the volume ratio of organic extractant to aqueous solution being in the range of 1–5:5;

incrementally transferring substantially free of said aqueous solution said organic extractant to an evaporating zone at a mildly elevated temperature containing a small absorbent disc, whereby a substantial proportion of said extractant is evaporated after each addition until completely evaporated and any of said drug present in said extractant is substantially quantitatively transferred to said disc;

introducing said disc into a scored area adjacent one end of a thin-layer chromatographic plate and developing said thin-layer chromatographic plate using a polar organic developing solvent containing a small amount of ammonium hydroxide;

drying said thin-layer chromatographic plate and treating said thin-layer chromatographic plate with formaldehyde, followed by dipping said thin-layer chromatographic plate into Mandelin's reagent, followed by washing said thin-layer chromatographic plate with water.

7. A method according to claim 6, wherein said inorganic salt is a mixture of sodium tungstate and sodium chloride, and said polar organic developing solvent has a major amount of ethyl acetate combined with a small amount of ammonium hydroxide.

8. A method according to claim 7, including the additional step of dipping the washed thin-layer chromatographic plate in modified Dragendorf's reagent.

9. A chromatographic method for detecting acidic and neutral drugs in a physiological medium which comprises:

agitating with a halocarbon containing organic extractant an aqueous solution of said physiological medium at an acidic pH having sufficient amount of zinc chloride to have a density greater than said organic extractant to transfer a substantial proportion of any of said drug to said extractant, said organic extractant consisting essentially of 40–60 volume percent chloroform, 15–20 volume percent alkanol of from 3 to 4 carbon atoms and 25 to 40 volume percent of an aliphatic hydrocarbon solvent of from 4 to 8 carbon atoms and the volume ratio of organic extractant to aqueous solution being in the range of 1–5:5;

incrementally transferring substantially free of said aqueous solution said organic extractant to an evaporating zone at a mildly elevated temperature containing a small absorbent disc, whereby a substantial proportion of said extractant is evaporated after each addition until completely evaporated and any of said drug present in said extractant is substantially quantitatively transferred to said disc;

introducing said disc into a scored area adjacent one end of a thin-layer chromatographic plate and developing said thin-layer chromatographic plate using a polar organic solvent containing a small amount of ammonium hydroxide;

drying said thin-layer chromatographic plate and treating said thin-layer chromatographic plate with diphenylcarbazone in chloroform, followed by treating successively with aqueous silver salt and aqueous mercuric salt solutions.

10. A method according to claim 9, wherein said polar organic developing solvent has a major amount of ethyl acetate.

11. A method according to claim 10, wherein said physiological medium is serum, which is combined with saturated aqueous zinc chloride and said polar organic developing solvent is a mixture of ethyl acetate and chloroform.

* * * * *